US012697151B2

(12) United States Patent
Klausman et al.

(10) Patent No.: US 12,697,151 B2
(45) Date of Patent: Aug. 4, 2026

(54) MODULAR TULIP UNLOCKER

(71) Applicant: Astura Medical Inc., Iriving, TX (US)

(72) Inventors: Keith Klausman, Irving, TX (US);
Thomas Purcell, Irving, TX (US)

(73) Assignee: ASTURA MEDICAL INC., Irving, TX
(US)

( * ) Notice: Subject to any disclaimer, the term of this
patent is extended or adjusted under 35
U.S.C. 154(b) by 0 days.

(21) Appl. No.: 18/961,386

(22) Filed: Nov. 26, 2024

(65) Prior Publication Data

US 2026/0144577 A1 May 28, 2026

(51) Int. Cl.
 *A61B 17/70* (2006.01)
 *A61B 17/86* (2006.01)
(52) U.S. Cl.
 CPC ...... *A61B 17/7076* (2013.01); *A61B 17/7032*
 (2013.01); *A61B 17/8685* (2013.01)

(58) Field of Classification Search
 CPC . A61B 17/70; A61B 17/7037; A61B 17/7032;
 A61B 17/7098; A61B 17/7044; A61B
 17/7076; A61B 17/86; A61B 17/8685
 See application file for complete search history.

(56) References Cited

U.S. PATENT DOCUMENTS

2018/0092679 A1 * 4/2018 Toon ................... A61B 17/7035
2022/0133360 A1 * 5/2022 Papenfuss .......... A61B 17/7076
 606/279

* cited by examiner

*Primary Examiner* — Christopher J Beccia
(74) *Attorney, Agent, or Firm* — Michael R Shevlin

(57) ABSTRACT

A modular tulip unlocker is disclosed that is designed to
unlock a modular tulip assembly coupled to a pedicle screw
to reestablish polyaxial movement to reposition the modular
tulip assembly, or to remove the modular tulip assembly
from the pedicle screw.

19 Claims, 8 Drawing Sheets

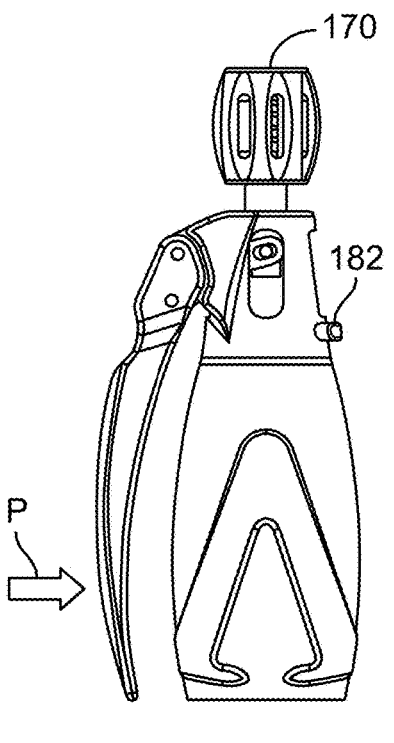
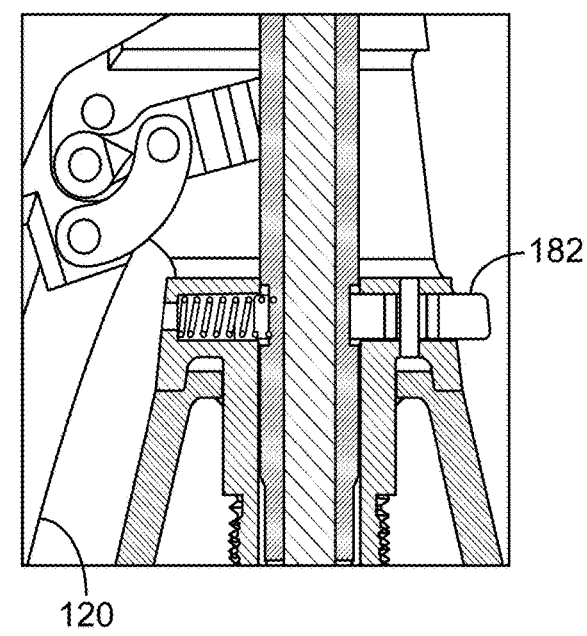
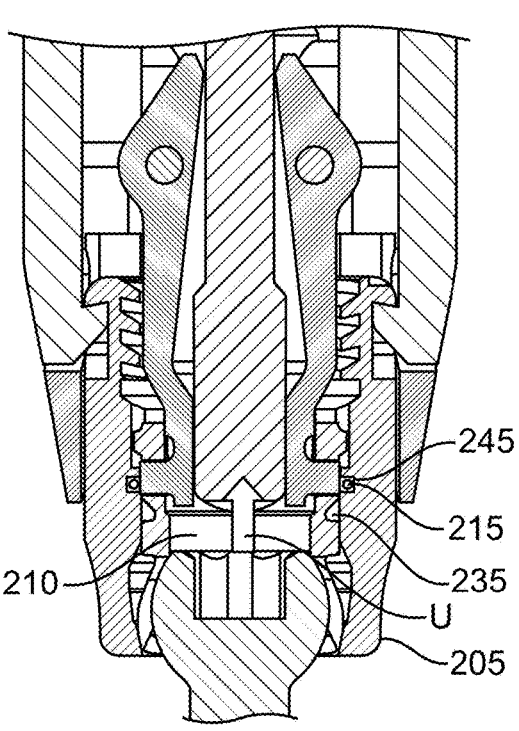
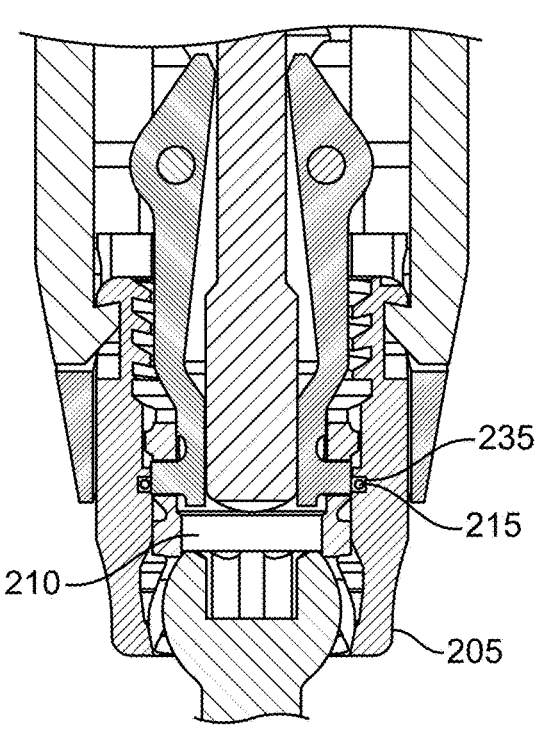
FIG. 13                 FIG. 14

MODULAR TULIP UNLOCKER

CROSS-REFERENCE TO RELATED APPLICATIONS

N/A.

FIELD

The present invention relates generally to the field of spinal fusion surgery, and more specifically, to a modular tulip unlocker used to unlock a modular tulip assembly from a pedicle screw shank.

BACKGROUND

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras. One known device is a stabilization rod interconnecting the two or more pedicle screws to stabilize the vertebras spanned by the pedicle screws. The pedicle screw includes a U-shaped channel for receiving the stabilization rod and a set pedicle screw to apply compressive force between the rod and the pedicle screwhead to firmly fix the rod between the spanned vertebras and thus stabilize the spinal vertebrae.

In some procedures, a modular tulip may be attached to a pedicle screwhead of a pedicle screw and locked on during the procedure, this allows maximum visibility of the site when using a minimally invasive approach and performing disc preparation.

In some cases, the modular tulip may need to be repositioned on the pedicle screw shank, or the modular tulip may need to be removed from the pedicle screw shank.

It may be desirable to provide an instrument to unlock the modular tulip from the pedicle screwhead to reestablish polyaxial movement or remove the modular tulip from the pedicle screwhead.

SUMMARY

The present invention is directed to a modular tulip unlocker that attaches to modular tulip assembly to reposition the modular tulip bushing within the modular tulip body to the unlocked state to reestablish polyaxial movement or to remove the tulip from the pedicle screw head.

According to some embodiments, the modular tulip unlocker comprises: tulip engagement clips having a distal end configured to attach to a modular tulip body; a proximal knob with a rotating knob shaft, wherein rotation of the proximal knob translates the rotating knob shaft down or up; a distal shuttle threadably engaged to the rotating knob shaft, the distal shuttle is configured to engage the modular tulip assembly and translation of the rotating knob shaft actuates the distal shuttle; and an actuation lever connected to an internal shaft configured to couple with the modular tulip bushing for upward translation of the modular tulip bushing.

According to some embodiments, the modular tulip unlocker comprises: tulip engagement clips having a distal end configured to attach to a modular tulip body; a proximal knob with a rotating knob shaft, wherein rotation of the proximal knob translates the rotating knob shaft down or up; a distal shuttle having pivoting shuttle members with distal push feet, the pivoting shuttle members having opposing ramps configured to slidingly engage the rotating knob shaft, the distal shuttle is configured to engage the modular tulip assembly and translation of the rotating knob shaft actuates the pivoting shuttle members with distal push feet; an actuation lever connected to an internal shaft configured to couple with the modular tulip bushing for upward translation and apply an upward force to lift the modular tulip bushing upward in the modular tulip body; and a lever return spring coupled to the internal shaft configured to: compress when the actuation lever is pulled, and expand when the actuation lever is released to return the actuation lever to the starting position.

According to some embodiments, the modular tulip unlocker comprises: tulip engagement spring-loaded clips configured to separate when inserted on a modular tulip body until the distal end is coupled to the modular tulip body to lock the modular tulip assembly on the distal end of the modular tulip unlocker; a proximal knob with a rotating knob shaft, wherein rotation of the proximal knob translates the rotating knob shaft distally or proximally; a distal shuttle configured to engage the modular tulip assembly having pivoting shuttle members with distal push feet, the pivoting shuttle members having opposing ramps configured to slidingly engage the rotating knob shaft rotating distally to slidingly engage the opposing ramps to push the pivoting members and distal push feet away each other and through lateral openings of the modular tulip bushing to compress flexible wires or spring pins to unlock the modular tulip bushing from the modular tulip body; an actuation lever connected to an internal shaft configured to couple with the modular tulip bushing for upward translation and apply an upward force to lift the modular tulip bushing upward in the modular tulip body, a force limiting spring positioned within an inline coupling attached to the internal shaft designed to limit the amount of upward force applied to the modular tulip bushing; and a lever return spring coupled to the internal shaft configured to: compress when the actuation lever is pulled, and expand when the actuation lever is released to return the actuation lever to the starting position.

BRIEF DESCRIPTION OF THE DRAWINGS

FIGS. 11-14 show the steps using the modular tulip unlocker to unlock the modular tulip assembly.

DETAILED DESCRIPTION

A modular tulip unlocker is disclosed that is designed to unlock a modular tulip assembly coupled to a pedicle screw to reestablish polyaxial movement to reposition the modular tulip assembly, or to remove the modular tulip assembly from the pedicle screw. The modular tulip unlocker attaches to modular tulip assembly and repositions the modular tulip bushing within the modular tulip body from a locked state to an unlocked state.

Figures 1, 2:
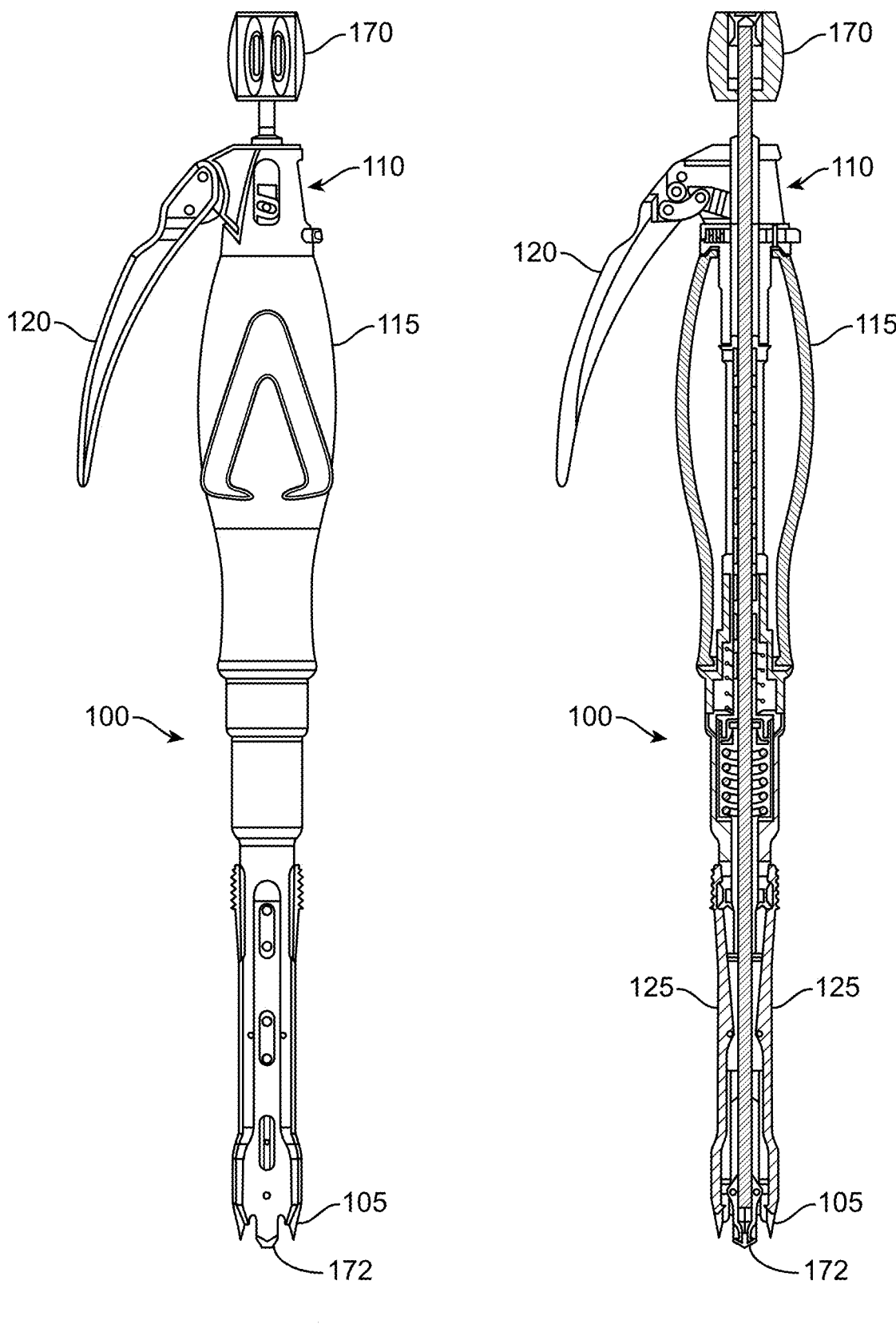
FIG. 1 is a side view showing one embodiment of a modular tulip unlocker attached to a modular tulip assembly.
FIG. 2 is a sectional side view of FIG. 1.

FIG. 1 is a side view showing one embodiment of a modular tulip unlocker 100 attached to a modular tulip assembly 200. The modular tulip unlocker 100 is configured to reposition a modular tulip bushing 210 to the unlocked state to reestablish polyaxial movement or to remove the tulip from a pedicle screw head. The modular tulip unlocker 100 includes a distal end 105 and a proximal end 110. The distal end includes spring-loaded clips 125 configured to couple with a modular tulip body, and a distal shuttle 172 configured to couple to the modular tulip assembly 200. The proximal end 110 includes a handle 115 to hold the modular tulip unlocker 100, an actuation lever 120 connected to an internal shaft for linear translation of a modular tulip bushing, and a proximal knob 170 threadably engaged to the distal shuttle 172.

FIG. 2 is a sectional side view of the modular tulip unlocker 100 showing the proximal knob 170 is threadably engaged to distal shuttle 172 with a rotating knob shaft. The distal shuttle is configured to engage the modular tulip assembly 200. Rotation of the proximal knob 170 also rotates the rotating knob shaft and actuates the distal shuttle 172 to engage flexible wires or spring pins to unlock the modular tulip bushing 210 to reestablish polyaxial movement of the modular tulip assembly 200 on the pedicle screw.

Figure 3:
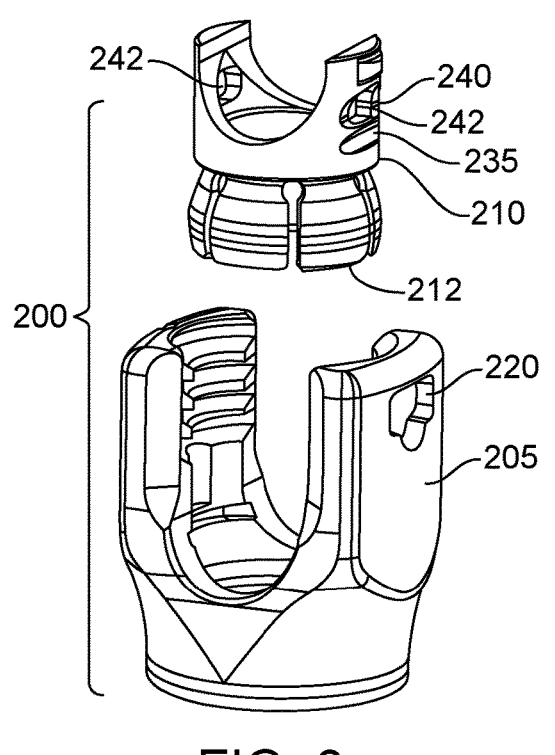
FIG. 3 is a perspective exploded view showing components of the modular tulip assembly.

FIG. 3 is a perspective exploded view showing components of the modular tulip assembly 200, including a U-shaped tulip body 205 and a modular tulip bushing 210. The modular tulip bushing 210 includes flexible members 212 around a lower opening configured to receive a pedicle screwhead, and a tapered distal external profile. Once the pedicle screw head 315 is within the flexible members 212, the tapered profile engages the inside of the U-shaped tulip body 205 and squeezes the pedicle screwhead 315 with the flexible members 212.

The modular tulip bushing 210 also includes two-stage cut outs on both sides, the first-stage cut outs are lower cut outs 235 and the second-stage cut outs are upper cut outs 240. When the lower cut outs 235 are coupled with the flexible wires 215, the modular tulip assembly 200 is in a delivery state or unlocked state with pedicle screwhead 315, allowing poliaxial movement. When the upper cutouts 240 are coupled with the flexible wires 215, the modular tulip assembly 200 is in a locked state with pedicle screwhead 315, preventing poliaxial movement. The lower and upper cut outs 235, 240 interact with spring pins or flexible wires

Figure 4:
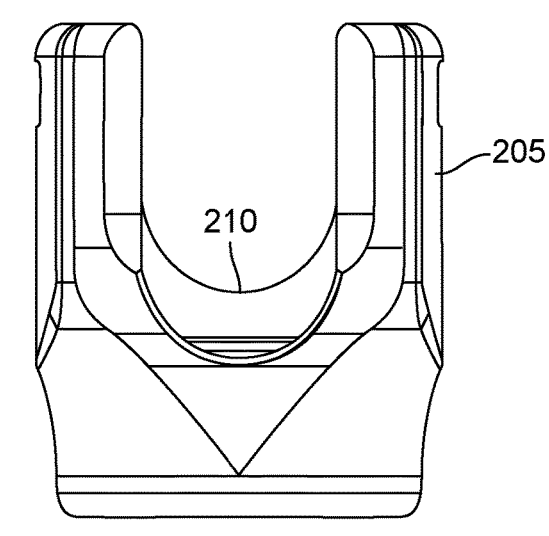
FIG. 4 is a side view showing the modular tulip bushing positioned within U-shaped tulip body.

215 to lock the modular tulip bushing 210 within the U-shaped tulip body 205 and prevent backout. (See FIGS. 7 and 8) FIG. 4 is a side view showing the modular tulip bushing 210 positioned within U-shaped tulip body 205. The figure shows the modular tulip assembly 200 in the delivery state or unlocked state, with the modular tulip bushing 210 unlocked within the tulip body 205.

Figure 5:
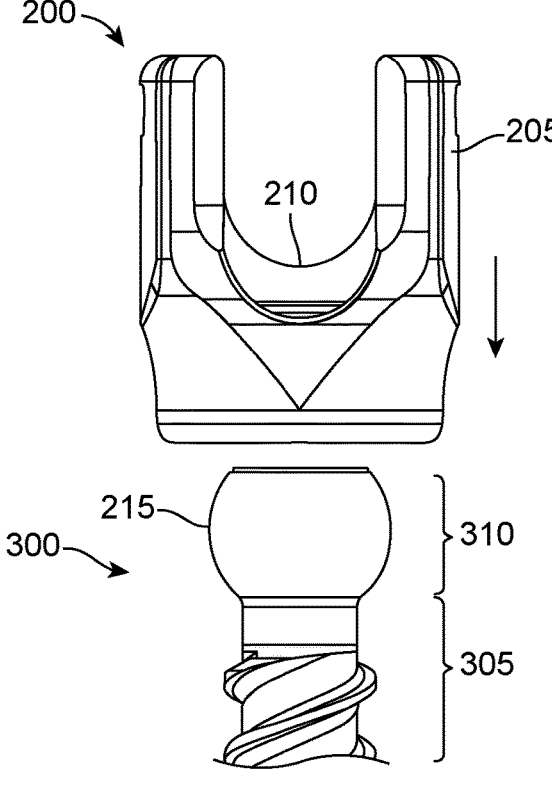
FIG. 5 is a side view showing modular tulip assembly being lowered on a pedicle pedicle screw that has been implated.

FIG. 5 is a side view showing unlocked modular tulip assembly 200 being lowered on a pedicle pedicle screw 300 that has been implated. The pedicle pedicle screw 300 includes a proximal end having a pedicle screwhead 310 with a curved outer surface 315 and a distal end having a pedicle screw shank 305. Once the pedicle screw shank 305 has been implanted, the surgeon selects a modular tulip assembly 200 from the various modular tulip assembly options. The modular tulip assembly 200 is positioned on the pedicle screwhead 210 in the unlocked state. Attaching the modular tulip 200 later in the surgery allows maximum visibility when using a minimally invasive approach.

Figure 6:
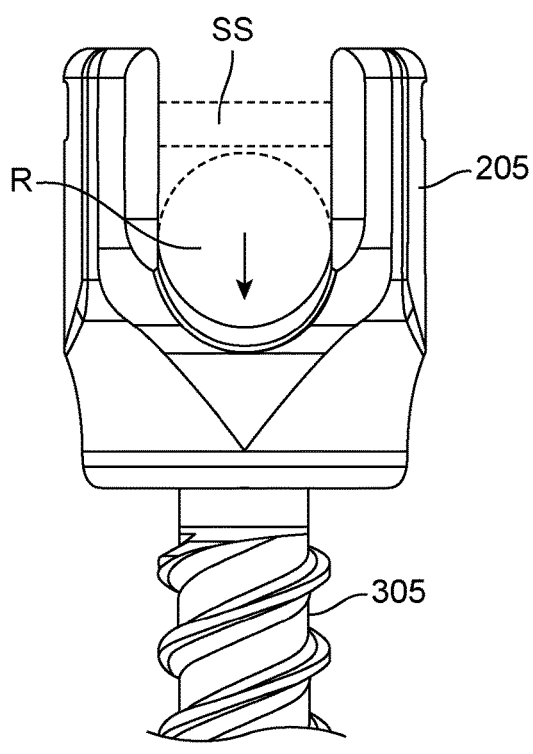
FIG. 6 is a side view of the modular tulip assembly in a locked state on the pedicle pedicle screw.

FIG. 6 is a side view of the modular tulip assembly 200 in a locked state on the pedicle pedicle screw 300. The interior of the U-shaped tulip body 205 includes a threaded portion to receive a rod locking device, such as a set pedicle screw SS. The rod R is positioned in the modular tulip assembly 200, and the set pedicle screw is configured to reduce the rod R into the U-shaped tulip body 205 and push the rod R 400

Figure 7:
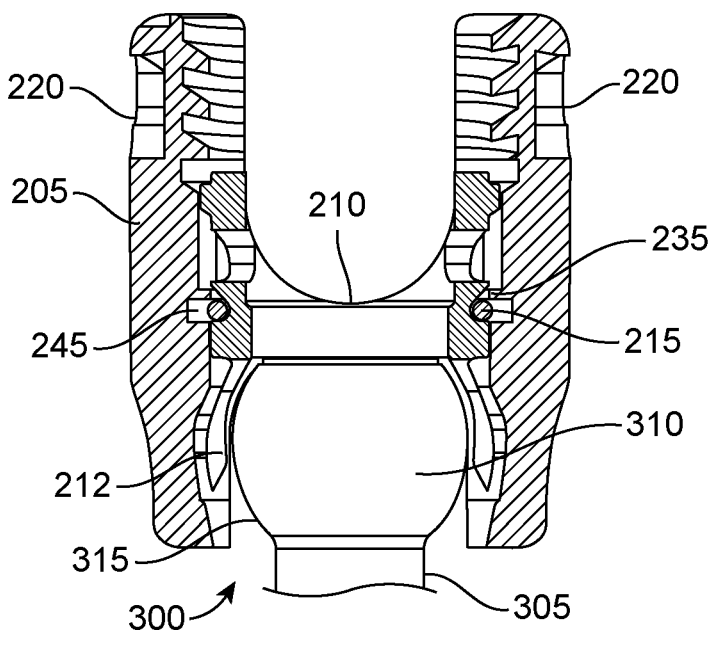
FIG. 7 is a sectional view of the modular tulip assembly in the unlocked state on a pedicle screw.

FIG. 7 is a sectional view of the modular tulip assembly 200 in the unlocked state on a pedicle screw 300. During assembly, the modular tulip bushing 210 is inserted into a central opening of the U-shaped tulip body 205. The modular tulip bushing 210 is configured to translate downward inside the U-shaped tulip body 205 to contact and flex or compress the flexible wires 215 into radial grooves in the wall of the U-shaped tulip body 205. In the first-stage, the flexible wires 215 spring back straight when they engage the lower cut outs 235 and prevent upward translation or backing out of the modular tulip bushing 210 from the U-shaped tulip body 205. The lower cut outs 235 include a lower portion that is shaped to engage the flexible wire 215 to prevent upward translation of the modular tulip bushing 210, and an upper ramped or tapered portion that is shaped to engage and flex or compress the flexible wire 215 into the grooved slot 245 to allow continued downward translation of the modular tulip bushing 210 from the first-stage to the second-stage. In the first-stage, the modular tulip assembly 200 is in an unlocked state within modular tulip bushing 210 configured to be pushed on a pedicle screwhead.

Figure 8:
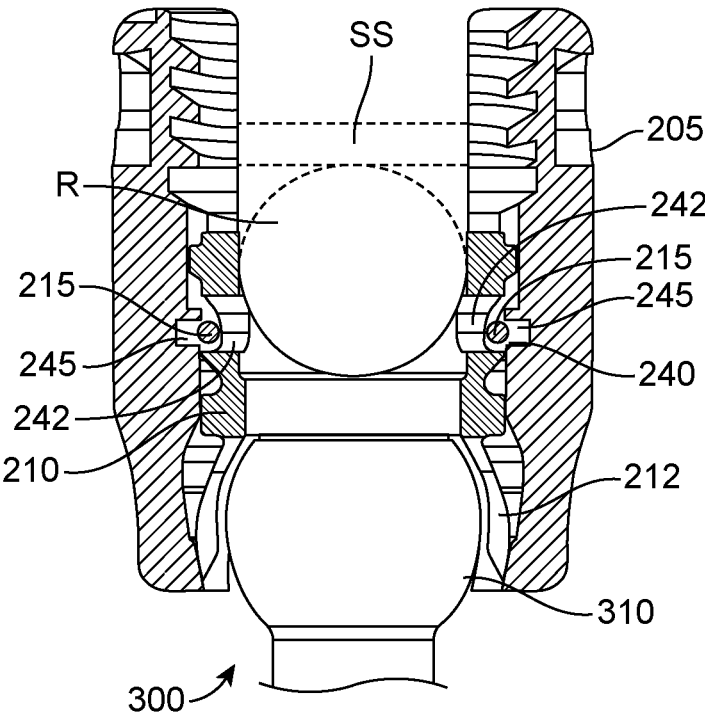
FIG. 8 is a sectional view of the modular tulip assembly in the locked state on the pedicle screw.

FIG. 8 is a sectional view of the modular tulip assembly 200 in the locked state on the pedicle screw 300. The flexible members 212 include a tapered distal external profile. Once the pedicle screwhead 315 is positioned within the flexible members 212, the modular tulip bushing 210 is translated downward. During this downward translation, the ramped portion of the lower cut outs 235 compress the flexible wire 215 into the groove slot 245 until it reaches the second-stage upper cut outs 240, then the flexible wire 215 enters the second-stage upper cut outs 240, locking the modular tulip bushing 210 in the secured or captured state. Also, during this downward translation, the tapered distal external profile of the flexible members 212 engage the inside of the U-shaped tulip body 205 and squeeze the pedicle screwhead 315 with the flexible members 212.

The second-stage upper cut outs 240 engage the flexible wire 215 that have been compressed by the ramped or tapered portion in the first-stage one as the modular tulip bushing 210 continues to translate downward into the U-shaped tulip body 205. The flexible wires 215 spring back straight when they engage the upper cut outs 240. The upper cut outs 240 include a lower portion that is shaped to engage the flexible wire 215 to prevent upward translation of the modular tulip bushing 210. In the second-stage, the modular tulip bushing 210 is in a locked state within the U-shaped tulip body 205 to secure and the pedicle screwhead is locked in the modular tulip assembly 200.

Flexible wires 215 may provide an audible sound and/or tactile feedback when transitioning the modular tulip bushing 210 from the unlocked state to the locked state. This feedback gives the surgeon confidence that the change from the unlocked state to the locked state was completed successfully. The flexible wire 215 also stops the modular tulip bushing 210 from upward translation back into the unlocked state, which eliminates the possibility of the modular tulip assembly 200 disengaging the pedicle screwhead 315 accidentally.

Figure 9:
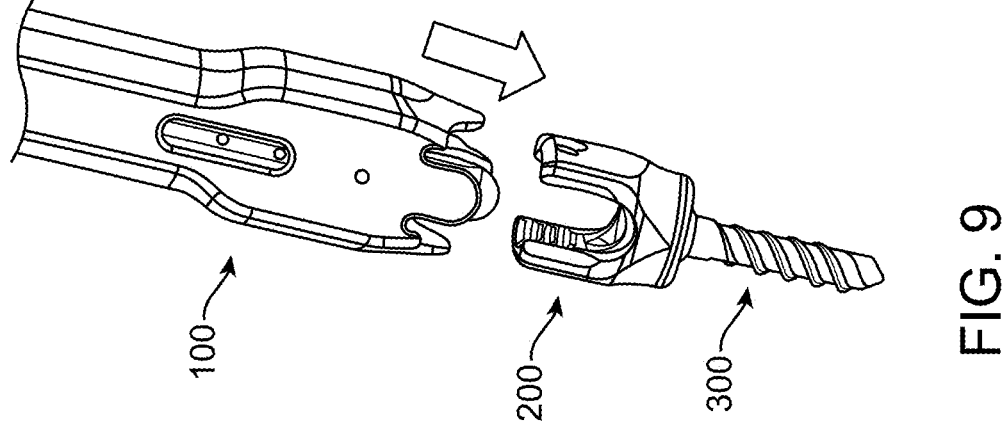
FIG. 9 is a perspective view showing the distal shuttle on the distal end of the modular tulip unlocker being inserted into the modular tulip assembly in a locked state on a pedicle screw.

FIG. 9 is a perspective view showing the distal shuttle 172 on the distal end 105 of the modular tulip unlocker 100 being inserted into the modular tulip assembly 200 in a locked state on a pedicle screw 300.

Figure 10:
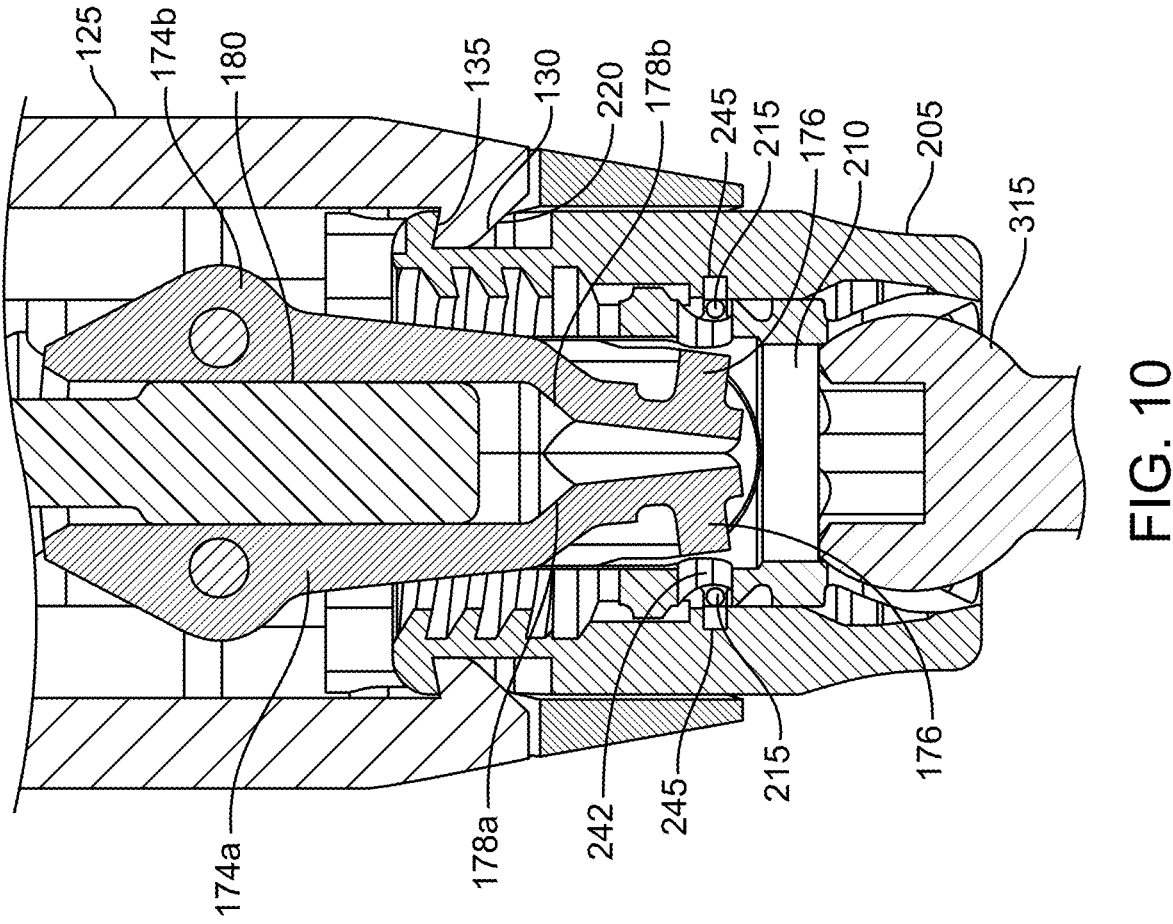
FIG. 10 is a sectional view showing the distal shuttle coupled with the modular tulip assembly mounted on a pedicle screw.

FIG. 10 is a sectional view showing the distal shuttle 172 coupled with the modular tulip assembly 200 mounted on a pedicle screw 300. The modular tulip unlocker 100 attaches to the modular tulip assembly 200 by way of spring-loaded clips 125 holding it in place. The spring-loaded clips 125 include ramped distal ends 130 configured to move the spring-loaded clips 125 apart when they slide on the tulip body 205. The spring-loaded clips 125 further include negative angle engagement tabs 135 and the tulip body 205 includes negative angle pockets 220. The spring-loaded clips 125 slide on the tulip body 205 until the negative angle engagement tabs 135 meet the negative angle pockets 220, then the negative angle engagement tabs 135 go into the negative angle pockets 220, locking the modular tulip assembly 200 on the distal end 105 of the modular tulip unlocker 100.

FIGS. 11-14 show the steps using the modular tulip unlocker 100 to unlock the modular tulip assembly 200. In summary, the proximal knob 170 is threadably engaged to a distal shuttle 172 with a rotating knob shaft 180. Rotating R the proximal knob 170 opens (clockwise) or closes (counter clockwise) the pivoting shuttle members 174a, 174b. The pivoting shuttle members 174a, 174b include distal push feet 176 sized to fit within lateral openings 242 of the modular tulip bushing 210. Once through the lateral openings 242, the distal push feet 176 contact and compress the flexible wires 215 into radial groove 245 within the modular tulip body 205. By moving the flexible wires 215 out beyond the modular tulip bushing 210, it allows for the instrument to lift the modular tulip bushing 210 into the unlocked state.

Figure 11:
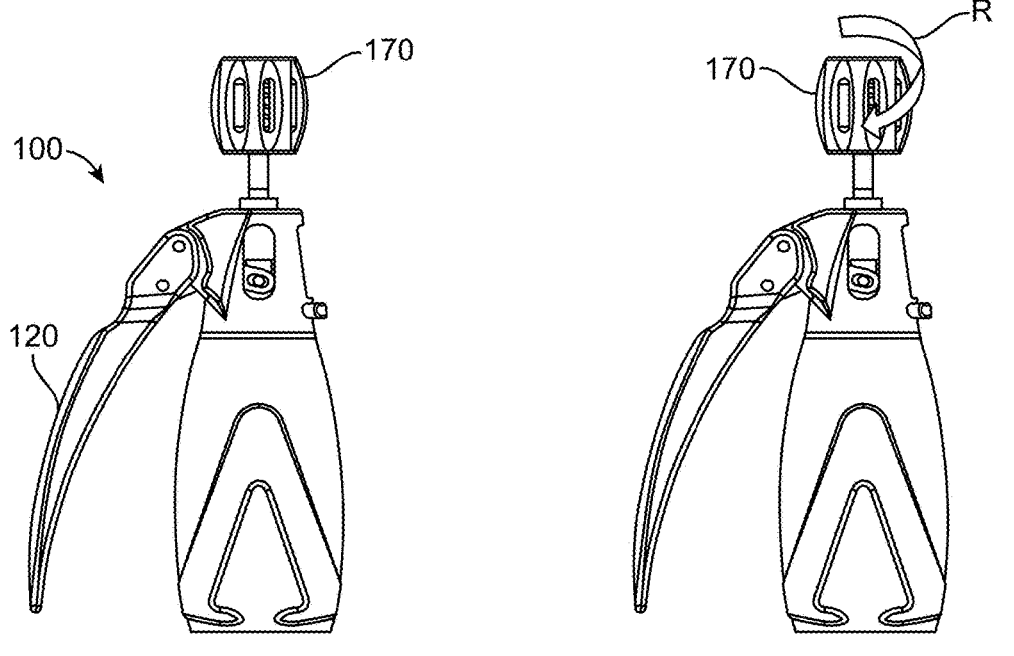

FIG. 11 is a view showing the modular tulip unlocker 100 attached to the modular tulip assembly 200 in a locked state with the flexible wires 215 positioned in the upper cut outs 240. The distal end 105 of the modular tulip unlocker 100 attaches to the modular tulip body 205 with spring-loaded clips 125, and the distal shuttle 172 engages the modular tulip bushing 210. The distal shuttle 172 includes pivoting shuttle members 174a, 174b with distal push feet 176 sized to fit within the lateral openings 242 in the modular tulip bushing 210. The pivoting shuttle members 174a, 174b include opposing ramps 178a, 178b configured to slidingly engage the rotating knob shaft 180.

Figure 12:
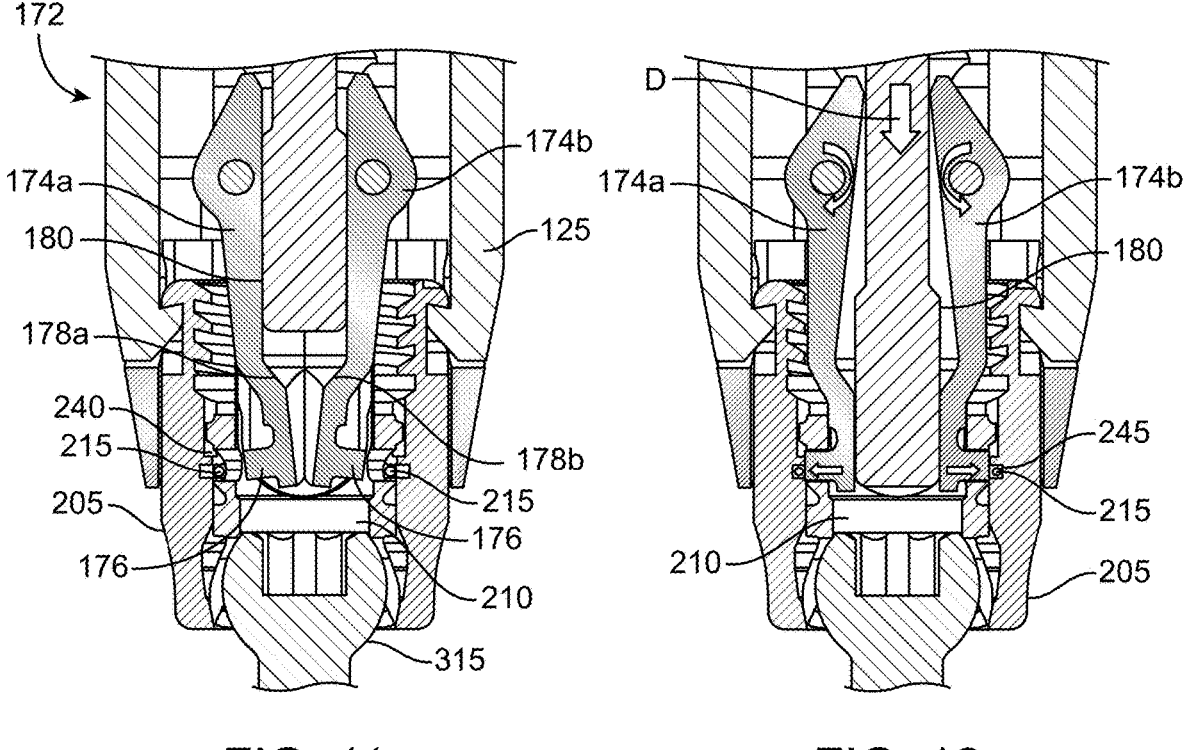

FIG. 12 is a view showing the distal feet 176 compressing the flexible wires 215 into radial grooves 245 in the wall of the U-shaped tulip body 205. Rotating R the proximal knob 170 clockwise translates the rotating knob shaft 180 distally D with the distal end slidingly engaging the opposing ramps 178a, 178b and rotating the pivoting shuttle members 174a, 174b away from each other. As the pivoting shuttle members 174a, 174b rotate away from each other, the push feet 176 extend through the lateral openings 242 of the modular tulip bushing 210 and compress the flexible wires 215 into radial groove 245 within the modular tulip body 205.

FIG. 13 is a view showing the modular tulip bushing 210 translating proximally P while the distal feet 176 press the flexible wires 215 in the radial grooves 245. The actuation lever 120 is connected to an internal shaft via a linkage which converts the actuation lever pull action to proximal translation of the internal shaft. When the actuation lever 120 is pulled P toward the handle, the internal shaft translates and lifts the modular tulip bushing 210 upward U away from the upper cut outs 240.

FIG. 14 is a view showing the modular tulip bushing 210 in the unlocked state with the flexible wires 215 in the lower cut outs 235. Once the actuation lever 120 is pulled completely, a spring-loaded latch 182 engages to hold the actuation lever 120 in place. The action of pulling the actuation lever 120, lifts the modular tulip bushing 210 to the unlocked state with the flexible wires 215 positioned in the lower cut outs 235.

Figures 15, 16, 17:
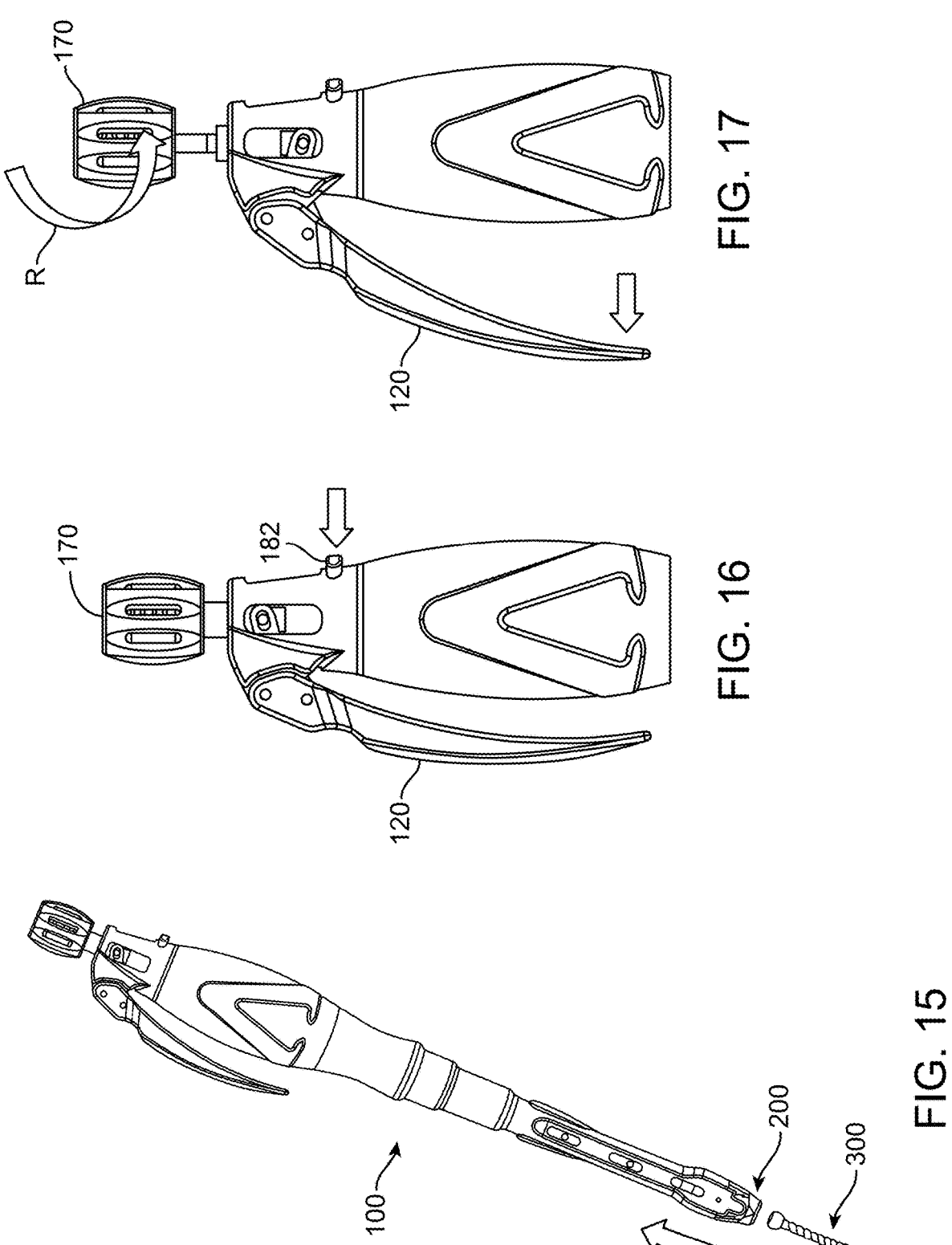
FIG. 15 shows the modular tulip assembly in the unlocked state being removed from the screw head.
FIG. 16 shows pushing the spring-loaded latch to disengage the actuation lever.
FIG. 17 shows the actuation lever being released and returning to the original position.

FIG. 15 shows the modular tulip assembly 200 in the unlocked state being removed from the screw head by pulling upwards on the modular tulip unlocker 100.

Once the modular tulip assembly 200 is removed from the screw head, the modular tulip assembly 200 may be removed from the modular tulip unlocker 100.

FIG. 16 shows pushing the spring-loaded latch 182 to disengage the actuation lever 120.

FIG. 17 shows the actuation lever 120 being released and returning to the original position. To remove the modular tulip assembly 200 from the modular tulip unlocker 100, the proximal knob 170 is rotated in the counterclockwise direction until a laser mark line is shown, or until the knob no longer rotates in the counter clockwise direction. This step translates the rotating knob shaft 180 proximally and disengages pivoting shuttle members 174a, 174b from the modular tulip bushing 210.

Figures 18, 19:
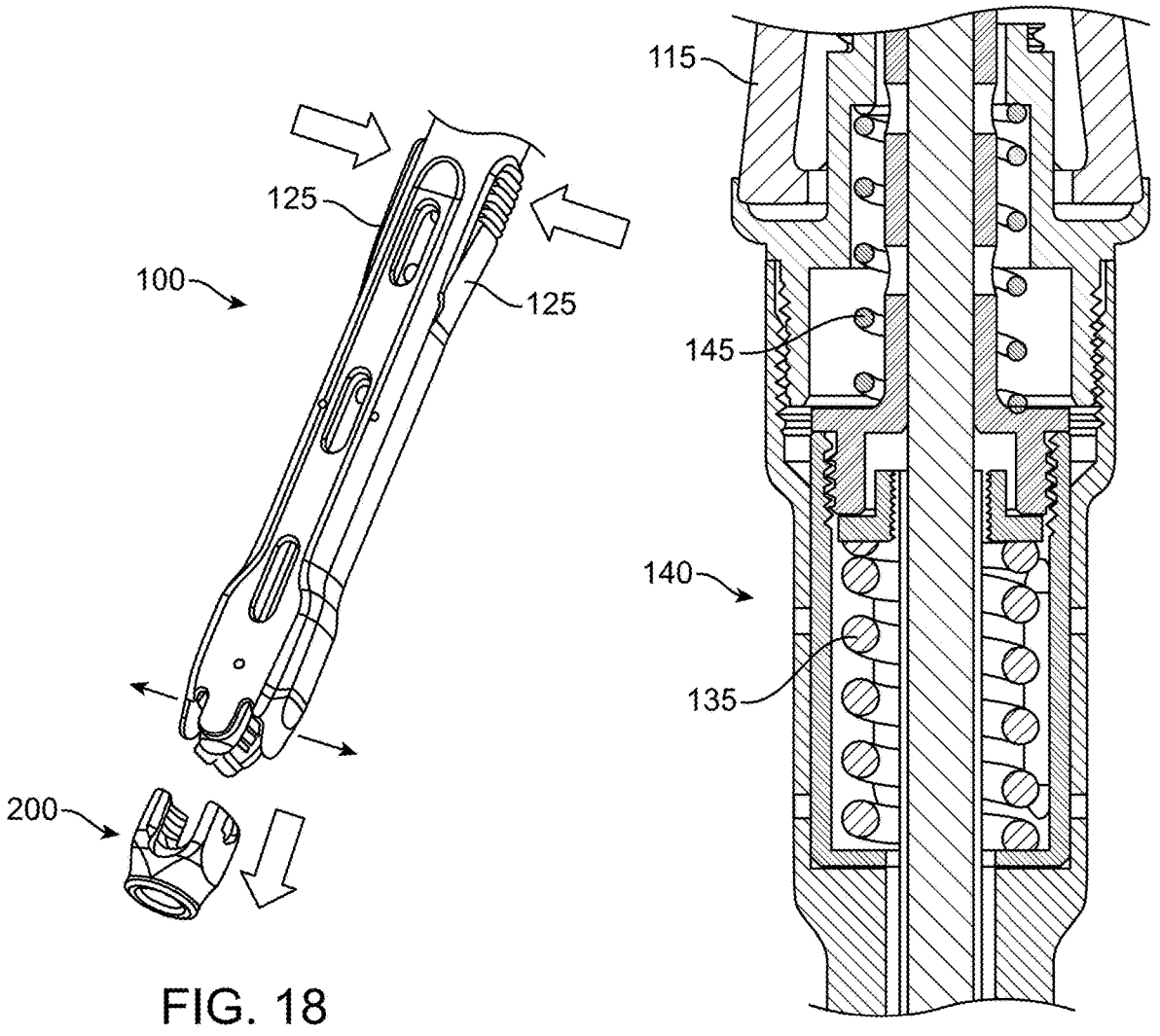
FIG. 18 shows compressing the proximal end of the spring-loaded clips releases the modular tulip assembly.
FIG. 19 shows a force limiting spring is positioned in an inline coupling attached to the internal shaft.

FIG. 18 shows compressing the proximal end of the spring-loaded clips 125 releases the modular tulip assembly 200, then pushing the proximal button to release the actuation lever.

FIG. 19 shows a force limiting spring 135 is positioned in an inline coupling 140 attached to the internal shaft. The force limiting spring 135 is designed to limit the amount of upward force generated on the modular tulip bushing 210 to avoid shearing the spring pins and pulling the bushing out of the tulip. An actuation lever return spring 145 may also be positioned in the inline coupling 140 attached to the internal shaft. The actuation lever return spring 145 is designed to compress when the actuation lever 120 is pulled. When the actuation lever 120 is released, the actuation lever return spring 145 expands and translates the internal shaft upward and returns the actuation lever 120 to the starting position.

The modular tulip unlocker 100 includes: a) Spring loaded clips 125 allowing for quick attachment/removal of the modular tulip assembly 200 on the modular tulip inserter 100; b) Silicone handle 115 with brake actuation lever style actuation lever 120 provides a controlled action of unlocking the modular tulip assembly 200; c) Threaded knob 170 engages/disengages the modular tulip assembly 200 and iv) Controlling the upward load applied to the modular tulip bushing 210 by way of load limiting spring 145.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A modular tulip unlocker designed to unlock a modular tulip assembly comprising:
   tulip engagement clips having a distal end configured to attach to a modular tulip body;
   a proximal knob with a rotating knob shaft, wherein rotation of the proximal knob translates the rotating knob shaft down or up;
   a distal shuttle threadably engaged to the rotating knob shaft, the distal shuttle is configured to engage the modular tulip assembly and translation of the rotating knob shaft actuates the distal shuttle;
   an actuation lever connected to an internal shaft configured to couple with the modular tulip bushing for upward translation of the modular tulip bushing; and
   a spring-loaded latch configured to hold the actuation lever in place after a complete pull.

2. The modular tulip unlocker of claim 1, wherein the distal shuttle includes pivoting shuttle members with distal push feet, the pivoting shuttle members having opposing ramps configured to slidingly engage the rotating knob shaft.

3. The modular tulip unlocker of claim 2, wherein actuating the distal shuttle includes rotating the proximal knob in a first direction to translate the rotating knob shaft distally to slidingly engage the opposing ramps and rotate the pivoting members and distal push feet away each other from a closed position to an open position.

4. The modular tulip unlocker of claim 3, wherein rotating the distal push feet away each other includes extending the distal push feet through lateral openings of the modular tulip bushing to compress flexible wires or spring pins to unlock the modular tulip bushing from the modular tulip body.

5. The modular tulip unlocker of claim 4, wherein rotating the proximal knob in a second direction translates the rotating knob shaft proximally to slidingly disengage the opposing ramps and rotate the pivoting members and distal push feet toward each other from the open position to the closed position.

6. The modular tulip unlocker of claim 5, wherein rotating the distal push feet towards each other includes withdrawal of the distal feet from the lateral openings of the modular tulip bushing to disengage the modular tulip bushing from the modular tulip shuttle.

7. The modular tulip unlocker of claim 5, wherein the rotating knob shaft includes a visual mark to indicate that the pivoting shuttle members are disengaged from the modular tulip bushing.

8. The modular tulip unlocker of claim 1, wherein the actuation lever is coupled to the internal shaft via a linkage which converts the pull action of the actuation lever to a linear translation of the internal shaft.

9. The modular tulip unlocker of claim 1, wherein a pull action of the actuation lever translates the internal shaft proximally to apply an upward force to lift the modular tulip bushing upward in the modular tulip body.

10. The modular tulip unlocker of claim 9, further comprising a force limiting spring positioned within an inline coupling attached to the internal shaft designed to limit the amount of upward force applied to the modular tulip bushing.

11. The modular tulip unlocker of claim 1, further comprising a lever return spring coupled to the internal shaft configured to:
   compress when the actuation lever is pulled, and
   expand when the actuation lever is released to return the actuation lever to the starting position.

12. The modular tulip unlocker of claim 1, wherein the tulip engagement clips are spring-loaded clips configured to separate when inserted on the modular tulip body until the distal end is coupled to the modular tulip body to lock the modular tulip assembly on the distal end of the modular tulip unlocker.

13. The modular tulip unlocker of claim 12, wherein pressing inward on a proximal end of the tulip engagement clips disengage the tulip engagement clips from the modular tulip body.

14. The modular tulip unlocker of claim 1, further comprising a handle on the proximal end configured to provides a controlled action of unlocking the modular tulip assembly.

15. A modular tulip unlocker designed to unlock a modular tulip assembly comprising:
   tulip engagement clips having a distal end configured to attach to a modular tulip body;
   a proximal knob with a rotating knob shaft, wherein rotation of the proximal knob translates the rotating knob shaft down or up;
   a distal shuttle having pivoting shuttle members with distal push feet, the pivoting shuttle members having opposing ramps configured to slidingly engage the rotating knob shaft, the distal shuttle is configured to engage the modular tulip assembly and translation of the rotating knob shaft actuates the pivoting shuttle members with distal push feet;
   an actuation lever connected to an internal shaft configured to couple with the modular tulip bushing for upward translation and apply an upward force to lift the modular tulip bushing upward in the modular tulip body; and
   a lever return spring coupled to the internal shaft configured to:
      compress when the actuation lever is pulled, and
      expand when the actuation lever is released to return the actuation lever to the starting position.

16. The modular tulip unlocker of claim 15, wherein actuates the pivoting shuttle members with distal push feet includes rotating the proximal knob in a first direction to translate the rotating knob shaft distally and slidingly engage the opposing ramps to push the pivoting members and distal push feet away each other and through lateral openings of the modular tulip bushing to compress flexible wires or spring pins to unlock the modular tulip bushing from the modular tulip body.

17. The modular tulip unlocker of claim 16, wherein rotating the proximal knob in a second direction translates the rotating knob shaft proximally to slidingly disengage the opposing ramps and rotate the pivoting members and distal push feet toward each other and withdraw from the lateral openings of the modular tulip bushing to disengage the modular tulip bushing from the modular tulip body.

18. The modular tulip unlocker of claim 16, further comprising a force limiting spring positioned within an inline coupling attached to the internal shaft designed to limit the amount of upward force applied to the modular tulip bushing.

19. A modular tulip unlocker designed to unlock a modular tulip assembly comprising:

tulip engagement spring-loaded clips configured to separate when inserted on a modular tulip body until the distal end is coupled to the modular tulip body to lock the modular tulip assembly on the distal end of the modular tulip unlocker;

a proximal knob with a rotating knob shaft, wherein rotation of the proximal knob translates the rotating knob shaft distally or proximally;

a distal shuttle configured to engage the modular tulip assembly having pivoting shuttle members with distal push feet, the pivoting shuttle members having opposing ramps configured to slidingly engage the rotating knob shaft rotating distally to slidingly engage the opposing ramps to push the pivoting members and distal push feet away each other and through lateral openings of the modular tulip bushing to compress flexible wires or spring pins to unlock the modular tulip bushing from the modular tulip body;

an actuation lever connected to an internal shaft configured to couple with the modular tulip bushing for upward translation and apply an upward force to lift the modular tulip bushing upward in the modular tulip body, a force limiting spring positioned within an inline coupling attached to the internal shaft designed to limit the amount of upward force applied to the modular tulip bushing; and a lever return spring coupled to the internal shaft configured to:

compress when the actuation lever is pulled, and expand when the actuation lever is released to return the actuation lever to the starting position.

\* \* \* \* \*